United States Patent [19]
Kanno et al.

[11] Patent Number: 5,374,715
[45] Date of Patent: Dec. 20, 1994

[54] METHOD FOR FORMING PROTEOLIPOSOME AND METHOD FOR FORMING GIANT PROTEOLIPOSOME

[75] Inventors: Tsunehiro Kanno, Isehara; Junji Ohyama, Yamato; Masanori Sakuranaga; Hiroyoshi Kishi, both of Atsugi; Nobuko Yamamoto, Isehara; Kinya Kato, Yokohama; Harumi Iwashita, Atsugi; Yasuko Tomida, Ebina, all of Japan

[73] Assignee: Canon Kabushiki Kaisha, Tokyo, Japan

[21] Appl. No.: 32,632

[22] Filed: Mar. 17, 1993

Related U.S. Application Data

[60] Division of Ser. No. 930,447, Aug. 19, 1992, Pat. No. 5,227,470, which is a continuation of Ser. No. 398,428, Aug. 25, 1989, abandoned.

[30] Foreign Application Priority Data

| Aug. 26, 1988 | [JP] | Japan | 63-211910 |
| Aug. 29, 1988 | [JP] | Japan | 63-215924 |
| Jul. 29, 1989 | [JP] | Japan | 1-197056 |
| Jul. 29, 1989 | [JP] | Japan | 1-197057 |

[51] Int. Cl.$^5$ ............... A61K 37/14; A61K 37/48; A61K 37/02
[52] U.S. Cl. ............... 530/402; 424/94.3; 424/450; 435/177; 435/188; 436/829; 530/812
[58] Field of Search ............... 210/500.27; 436/829; 514/2, 7, 8, 12, 21; 435/174, 177, 188; 424/94.3, 450; 530/350, 359, 400, 401, 402, 812

[56] References Cited

U.S. PATENT DOCUMENTS

| 4,532,089 | 7/1985 | MacDonald | 436/829 |
| 4,663,161 | 5/1987 | Mannino et al. | 424/89 |
| 4,873,089 | 10/1989 | Scotto et al. | 424/450 |

(List continued on next page.)

FOREIGN PATENT DOCUMENTS 8908130 9/1989 WIPO.

OTHER PUBLICATIONS

Biochim. Biophys. Acta, vol. 886, issued 1986, Salord et al, "Targeting of liposomes by covalent coupling . . . ", pp. 64–75.

Biochem. Biophys. Acta, vol. 810, issued 1985, Bokranz et al, "Phosphorylation and phosphate–ATP exchange . . . ", pp. 332–339.

Biochim. Biophys. Acta, vol. 814, issued 1985, Derksen et al, "An improved method for the covalent coupling of proteins to liposomes", pp. 151–155.

FEBS Letters, vol. 154, No. 1, issued Apr. 1983, Pabst et al, "Light-driven proton transport of bacteriorhodopsin . . . ", pp. 5–9.

J. Biol. Chem., vol. 262, No. 10, issued 25 May 1977, Eytan et al, "Selective Incorporation of Membrane Proteins into Proteoliposomes . . . ", pp. 3208–3213.

"Reassembly of protein–lipid complexes into large bilayer vesicles: Perspectives for membrane reconstitution," A. Darszon et al., Proc. Natl. Acad. Sci. U.S.A., vol. 77, No. 1, Jan. 1980, pp. 239–243.

(List continued on next page.)

Primary Examiner—Jeffrey E. Russel
Attorney, Agent, or Firm—Fitzpatrick, Cella, Harper & Scinto

[57] ABSTRACT

A method for forming a proteoliposome comprises incorporating into a liposome a membrane protein combined with a carrier. Further, a method for preparing a giant proteoliposome, comprises freezing and thawing an alkali metal salt solution containing a membrane protein and a lipid, and subsequently dialyzing against a second salt solution or a buffer solution having a lower osmotic pressure than that of said alkali metal salt solution. Further, a method for forming a proteoliposome, comprises by freezing and thawing an alkali metal salt solution containing a membrane protein combined with a carrier and a lipid.

13 Claims, 2 Drawing Sheets

U.S. PATENT DOCUMENTS

| | | | |
|---|---|---|---|
| 4,965,174 | 10/1990 | Arai et al. | 430/340 |
| 5,041,224 | 8/1991 | Ohyama et al. | 210/500.27 |
| 5,288,517 | 2/1994 | Kanno et al. | 436/829 |

OTHER PUBLICATIONS

"Saibou Kouga Ku (Cell technology)," vol. 7, No. 1, 1988 p. 94.

"The spontaneous incorporation of proteins into pre-formed bilayers," M. K. Jain et al., Biochemica et Biophysica Acta 906 (1987), pp. 33–68.

"The Isolation and Purification of Osmotically Intact Discs from Retinal Rod Outer Segments," H. G. Smith et al., Exp. Eye Res. (1975) vol. 20, pp. 211–217.

"Isolation of the Cell Membrane of *Halobacterium halobium* and its Fractionation into Red and Purple Membrane," D. Oesterhelt et al., Methods of Enzymology (1974) vol. 31, pp. 667–678.

"Preparation of Liposomes," N. Oku, Setsunan University, Osaka, Japan, pp. 528–549.

"Delipidation of bacteriorhodopson and reconstitution with exogenous phospholipid," K. Huang et al., Proc. Natl. Acad. Sci. USA, vol. 77, No. 1 Jan. 1980, pp. 323–327.

"Immunological Probes for Bacteriorhodopsin," K. Kimura et al., The Journal of Biological Chemistry, vol. 267, No. 6, pp. 2859–2867.

"Biochemical aspects of the visual process part 33 a convenient purification procedure of rhodopsin by means of affinity chromatography," Van Breugel et al., STN File Server, File BIOSIS, vol. 77, No. 231471, Abstract.

"Reactivity with lectins of the saccharide components of rhodopsin in reconstituted membranes. Orientation of the carbohydrates," S. Ishiguro et al., STN File Server, File Medline, Acc. No. 85122723.

"Reconstituted D-Glucose Transport fromt he Adipocyte Plasma Membrane. Chromatographic Resolution of Transport Activity from Membrane Glycoproteins Using Immobilized Concanavalin A," C. Carter-Su et al., American Chemical Society, vol. 19, 1980, pp. 2374–2385.

"Pump and displacement currents of reconstituted ATP synthase on black lipid membranes," B. Christensen et al., STN File Server, File CA vol. 111, No. 13, 1988, Acc. No. 111129d.

METHOD FOR FORMING PROTEOLIPOSOME AND METHOD FOR FORMING GIANT PROTEOLIPOSOME

This application is a division of application Ser. No. 07/930,447, filed Aug. 19, 1992, now U.S. Pat. No. 5,227,470, issued Jul. 13, 1993, which in turn, is a continuation of application Ser. No. 07/398,428, filed Aug. 25, 1989, now abandoned.

BACKGROUND OF THE INVENTION

1. Field of the Invention

The present invention relates to a method for forming a proteoliposome which has a membrane protein incorporated in a membrane of a vesicle such as or a liposome, and particularly to a method for forming a proteoliposome in which a membrane protein is incorporated in a manner so as to control molecular orientation.

The present invention also relates to a method for preparing a giant proteoliposome having a diameter of 5 $\mu$m or more in a simple process and in a large quantity under mild conditions.

The present invention further relates to a method for forming a giant proteoliposome having a membrane protein incorporated in a preferable molecular orientation.

2. Related Background Art

A liposome is an assembly of biologically functional molecules and is formed by dispersing and re-associating a lipid, which is a biomembrane-constituting molecule, in an aqueous solution and has a structure like a cellular membrane. The application of the liposome is under investigation as applied to medical diagnosis and treating medicines in medical care, and to production of useful materials in industrial fields.

The proteoliposomes which have a protean incorporated into the above mentioned liposomes can have a further higher function in addition to the function of the liposome because a functional molecule can be added thereto.

Proteoliposomes are prepared by various known methods corresponding to the uses thereof and the types of the protein. The known methods include a dialysis method, a sonication, a freeze-thaw method; etc.

In the dialysis method, a protein is solubilized together with a lipid by use of a detergent, and then the detergent is removed by dialysis to give small proteoliposomes having a diameter of 100 nm or less. In the sonication method, a protein is treated with a liposome by sonication, which gives small proteoliposomes having a small diameter of 100 nm or less also. In the freeze-thaw method, a mixed solution of a protein and a liposome is frozen and thawed repeatedly to incorporate the protein into a lipid membrane, which gives a relatively large proteoliposome of several hundred nm in diameter.

On the other hand, there is a biomembrane comprising a membrane protein embedded with preferable molecular orientation. Such anisotropic membrane constitution realizes vectorial transfer of a substance or of information such as reception and conduction of excitation, and transportation of a substance. Hence, in applications of the proteoliposome to medical treatment and industry as well, a constant orientational incorporation of the membrane protein is advantageous to realize the function effectively.

Conventional methods for producing proteoliposomes are based on the process of chemical or physical dissolution or partial destruction of a lipid membrane, and subsequent reconstruction of a membrane with inclusion of a membrane protein. In the process, no means for positively controlling the molecular-orientation of the membrane protein is achieved.

Practically, in proteoliposome membranes prepared by conventional methods, the proteins are incorporated with random orientation.

Further, the diameter of the proteoliposomes depends on the respective method of preparation, and cannot be optionally selected.

Detailed studies on inclusion of a membrane protein, especially a protein inherent in cellular membrane, into a lipid bilayer membrane in the formation of a proteoliposome is found only in exceptional reports such as "Zakim: Biochimica et Biophysica Acta, 906, 33–68 (1987)" which discloses that a spontaneous insertion of a membrane protein solubiltzed by a detergent or a membrane protein free from both the detergent and membrane lipid into a lipid bilayer membrane may occur under appropriate conditions with activation energy lower than that of fusion between liposomes, regarding cytochrome, UDP glucuronosyltransferase, bacteriorhodopsin, etc. The inserted protein, however, is not preferably oriented, and is not orientationally controlled at all.

On the other hand, a giant proteoliposome having a diameter of 5 $\mu$m or more is applicable as an artificial cell because it has a size equivalent to a cell and therefore can easily mimic various functions of the cell.

Its larger inner volume gives the advantages of a higher efficiency of substance retention, a higher efficiency of substance incorporation, etc. which allows development of high-performance micro-capsules, and chemical sensors, etc. Further, the size exceeding 5 $\mu$m in diameter thereof enables easy observation with an optical microscope and permits mechanical operation by means of micromanipulation or microinjection, which is hopefully adaptable to applications inherently different from the conventional proteoliposomes having smaller diameters.

Heretofore, known preparation methods of giant proteoliposomes have been limited to only a few methods such as an electric field fusion method and a giant liposome preparation method, none of which is practical.

The known methods for preparation of giant proteoliposomes, including an electric field fusion method, a stationary hydration method, a reverse phase evaporation method, and a freeze-thaw method are all under severe restriction, and are impractical except for restricted applications.

In the electric field fusion method, a suspension of small-diameter proteoliposomes prepared preliminarily in the conventional method is subjected to application of an electric field, leading to formation of giant proteoliposomes by aggregating and fusing the proteoliposomes. This method has the disadvantages that a low ionic concentration of the solution needs to be maintained because of the high electric field required, that only a small number of giant proteoliposomes can be prepared in one operation, and, further, that the diameter of proteoliposomes suitable for the fusion are limited and their preparation is not easy.

The stationary hydration method and the reverse phase evaporation method are both based on the application of a method for preparation of a giant liposome. The stationary hydration method which hydrates a thin lipid film formed on a glass wall under low ion strength to give a giant liposome, has serious disadvantages in that the ionic concentration of the solution should be $10^{-4}$M or less and, further that the presence of a protein inhibits the formation of a proteoliposome. Thus this method is difficult for wide applications. The reverse phase evaporation method which employs an emulsion formed by mixing a solution containing a protein with an ether solution of a lipid tends to cause denaturation or deactivation of the protein, and thus incorporatable proteins are strictly limited.

The freeze-thaw method which has been employed for reconstruction of a membrane protein and is applicable to preparation of a proteoliposome having a diameter of 1 $\mu$m or less, is known to be able to form only a small amount of giant proteoliposomes of 5–10 $\mu$m in diameter, but is of no practical use because of the limited small number and the small diameter of the particles.

As mentioned above, few methods are applicable in the preparation of giant proteoliposomes. All of the methods are strictly restricted and thus are not suitable for practical preparation. Accordingly, development of a method is desired which enables the preparation of a large amount of proteoliposomes by a simpler process under milder conditions.

Moreover, also for the giant proteoliposomes, a method is desired which allows the membrane protein to be incorporated into the membrane with the orientation of the membrane protein.

SUMMARY OF THE INVENTION

An object of the present invention is to provide a novel method for preparing a proteoliposome comprising a process for controlled orientation of a membrane protein differentiating the inside and the outside of the vesicle so that the incorporated membrane protein may be effectively utilized.

Another object of the present invention is to provide a method for forming a giant proteoliposome.

A further object of the present invention is to provide a method for forming a giant proteoliposome which contains a membrane protein incorporated therein with a controlled orientation.

According to an aspect of the present invention, a method is provided for forming a proteoliposome, comprising incorporating a membrane protein combined with a carrier into a liposome.

According to another aspect of the present invention, a method is provided for preparing a giant proteoliposome, comprising freezing and thawing an alkali metal salt solution containing a membrane protein and a lipid, and subsequently dialyzing against a second salt solution or a buffer solution having a lower osmotic pressure than that of the alkali metal salt solution to form a giant proteoliposome.

According to a further aspect of the present invention, a method is provided for preparing a giant proteoliposome, comprising freezing and thawing an alkali metal salt solution containing a membrane protein combined with a carrier and a lipid, and subsequently dialyzing against a second salt solution or a buffer solution having a lower osmotic pressure than that of the alkali metal salt solution to incorporate the membrane protein into a liposome.

According to a still further aspect of the present invention, a method is provided for preparing a Giant proteoliposome, comprising freezing and thawing an alkali metal salt solution containing a membrane protein combined with a carrier and a lipid, and subsequently dialyzing against a second salt solution or a buffer solution having a lower osmotic pressure than that of the alkali metal salt solution by separating the membrane protein from the carrier to incorporate the membrane protein into a liposome.

According to a still further aspect of the present invention, a method is provided for forming a proteoliposome, comprising freezing and thawing an alkali metal salt solution containing a membrane protein combined with a carrier and a lipid to incorporate the membrane protein into a liposome.

DETAILED DESCRIPTION OF THE PREFERRED EMBODIMENTS

One aspect of the present invention is to provide a method for forming a proteoliposome which comprises the steps of modifying a membrane protein with a carrier, subsequently mixing it with a liposome liquid dispersion to incorporate the membrane protein into the liposomes, and further separating the membrane protein from the carrier.

The liposome, a component of the proteoliposome can be prepared in various ways according to the constituting lipid, solution conditions, etc. in an optional size within the range of from several decade nm to several hundred $\mu$m. The inventors of the present invention became aware of the possibility of preparing a proteoliposome having a desired diameter thereof, and controlled orientation of the protein provided that a membrane protein could be inserted into a preliminarily prepared liposome with preferable orientation.

The inventors of the present invention, studying various modification of membrane proteins, found that modification of a membrane protein by an appropriate carrier limits the portion of the membrane protein capable of being inserted into a lipid bilayer membrane and enables the control of the orientation of the membrane protein, and have produced the present invention.

The method for forming a proteoliposome of the present invention is characterized in that specific sites of hydrophilic side chains of a membrane protein are modified with a carrier which will not enter the lipid bilayer membrane, and thereafter the membrane protein is mixed with a liposome dispersion preliminarily prepared. The membrane protein combined with a carrier is incorporated into the lipid bilayer membrane with the limited inserted portions, thus allowing the incorporation into the membrane with retention of a certain orientation.

In the present invention, any liposome can be employed which is capable of incorporating the membrane protein, and the diameter, lipid composition, etc. of the liposome can be selected optionally since the step of incorporation of the membrane protein into the liposome is independent of the step of formation of the liposome.

Accordingly, the orientation of the membrane protein can be controlled as desired in a proteoliposome having any diameter by selecting the site of the membrane protein modified by a carrier and the method of preparation of the liposome. The resulting membrane protein is incorporated into the proteoliposome in a direction of "right-side-out" or "inside-out".

The membrane protein in the present invention may have hydrophilic side chains, existing in the biomembrane, particularly an intrinsic membrane protein existing through the biological membrane. Additionally, a natural or synthetic peptide may also be employed if it can enter the membrane.

The specific examples of the membrane protein are: metabolism-catalysing enzymes such as a cytochrome oxidase, a cytochrome P-450, a membrane bound phospholipase, and an ATP synthesizing enzyme: channels which transport substances through a membrane such as a potassium channel, a sodium channel, and a calcium channel; pumps such as a sodium-potassium pump, and a proton pump; photoreceptive chromoproteins for reception and conduction of biological information such as rhodopsin and bacteriorhodopsin; neurotransmitter receptors such as an acetylcholine receptor and a glutamate receptor; hormone receptors such as a thyroid-stimulating hormone (TSH) receptor, and a glucagon (GC) receptor; and the like.

Such membrane proteins which are generally insoluble in water, and some of which accompany a membrane lipid may be employed as they are, or as a solution in a detergent within the range of controllability of the orientation by the modified carrier.

At a higher ratio of the membrane protein to the lipid, the remaining unincorporated amount of the membrane protein will increase practically, contrary to the expectation of a higher amount of incorporation. Therefore, it is desirable that the ratio of the protein to the lipid by weight is 1:1 at the highest, preferably within the range of from 1:10 to 1:100, The concentration of the lipid at the formation of liposome is preferably in the range of from 1 to 20 mM (0.75 to 15 mg/ml) depending on the method of preparation.

Any liposome may be employed in the present invention provided that it is capable of incorporating a membrane protein and of taking a bimolecular lamella structure. The examples are phospholipids, glycolipids, neutral lipids, etc. A synthetic bilayer-forming lipid may be employed which is not produced naturally. Various additives may also be added within a range so that the bilayer structure is not destroyed.

The size and the lipid composition of the liposome may be optionally selected without a special restriction.

Such liposomes may be formed from various lipids and addition products thereof by methods capable of forming a liposome of optional diameter. The methods include, for example, a sonication treatment, a detergent-dialysis method, a freeze-thaw method, and a reverse phase evaporation method. (See, for example, Zoku-Seikagaku Jikken Koza (Supplemental Textbook on Biochemical Experiment), Volume 3, "Membrane Lipid and Serum Lipoprotein (Continued)", edited by Biochemical Society of Japan, published by Tokyo Kagaku Dojin (1987).)

The carriers for modifying the membrane protein employed are those having a property of not entering the lipid bilayer membrane. For this purpose in the present invention, the carriers are employed which have a volume equal to or larger than the volume of the liposome prepared preliminarily. The shape of the carrier is not limited. For example, the carrier may be in a spherical shape having a diameter equal to or larger than that of the preliminarily prepared liposome, or may be planar, or of a curved shape having a radius of curvature equal to or larger than the radius of the preliminarily prepared liposome.

Liposomes usually have diameters of several ten nm to 1 $\mu$m, and some larger ones have diameters of 10 $\mu$m to several hundred $\mu$m. Thus the size of the carrier may be 1 $\mu$m to 10 $\mu$m, and 100 $\mu$m to 1 mm corresponding to the above diameters of the liposomes. The shape of the carrier need not be spherical as mentioned above. Any other shape of the carrier may be used. Continuous curved surfaces and inside surfaces of hollow tubes are also included in the carriers defined in the present invention.

The modification (or combination) of the specific portion of the hydrophilic side chain of the membrane protein with the carrier and the dissociation thereof is preferably conducted under mild conditions so that the protein may not be denatured.

For this purpose, a chromatographic technique for proteins may be applicable. The chromatography for proteins is intended to purify proteins, wherein combination and dissociation of a suitably modified carrier and a protein are conducted by use of electrostatic attraction (ion exchange chromatography), hydrophobic interaction (hydrophobic chromatography), hydrogen bonding (hydrogen bond chromatography), specific affinity (affinity chromatography), etc.

Carriers made of a material capable of causing the above-mentioned interaction and modifying a specific portion of the hydrophilic side chain of the membrane protein may be employed in the present invention: for example, the material having on the surface an active functional group such as an amino group, a hydroxyl group, an epoxy group, and a sulfylsulfide group. Specific examples of the carriers are gels such as of agarose, cellulose employed in chromatography; organic materials such as plastics; inorganic materials such as glass having oxygen on the surface, ceramic and metal oxide surfaces capable of being activated by cyanogen bromide and so forth. Among them, gels for chromatography are easily handled because the gels usually have a diameter of approximately 10 $\mu$m, and may be used with a column for protein chromatography. In some cases, the purification of a membrane protein and the reconstruction of the proteoliposome may be simultaneously performed.

The dissociation of the membrane protein incorporated into the liposome from the carrier may be performed by adding to the column a substance antagonistically acting on the combination of the carrier with the membrane protein, or by changing the physicochemical condition (such as pH, and salt concentration) of the solution, and so forth.

In an example of the former method, utilizing sugar portions existing at the end portions of most of membrane proteins, and a carrier bonded with a protein lectin having an ability to combine with sugar, the addition of excess sugar antagonistically combines with lectin to liberate the membrane protein. In another example, in a site specific combination of a monoclonal antibody with a specified portion of the membrane protein, utilizing an antigen-antibody reaction, the addition of excessive amount of hapten can dissociate antagonistically the membrane protein from the carrier. However, the bonding between an antigen and an antibody is so strong that the dissociation is not easy even with a large excess of the hapten, and moreover, preparation of a large amount of hapten is often difficult. Therefore, the method using lectin is more advantageous.

The methods of changing the physicochemical condition of the solution are considerably restricted in the application, since the proteoliposomes formed may often be destroyed by the change in the physicochemical condition.

The process of formation of proteoliposome of the present invention is schematically illustrated by FIGS. 1A to 1D, 2A and 2B and 3, in which like-numbered elements of the drawings are the same.

FIG. 1A to 1D illustrate schematically the fundamental principle of a method for forming a proteoliposome of the present invention. In the Figures, the treatment is performed through the steps of FIGS. 1A to 1D. First, a specific portion of the hydrophilic side chain of the membrane protein 2 is modified by and combined with the carrier 1. Second, a liquid dispersion of a liposome 3 is mixed with the membrane protein 2 supported by the carrier 1 to incorporate the membrane protein into the liposome, and subsequently the membrane protein 2 is dissociated from the carrier 1 to form a proteoliposome 4.

Figure 1A:
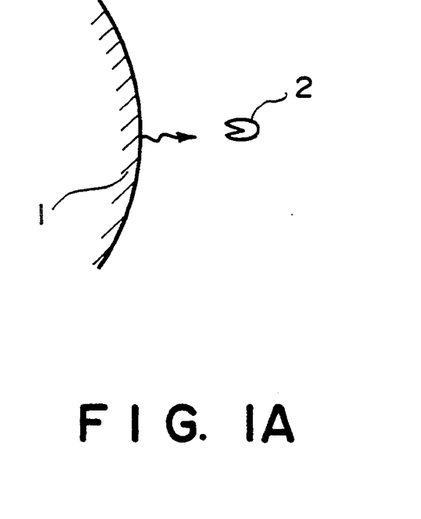
FIGS. 1A to 1D illustrate schematically the fundamental principle of a method for forming a proteoliposome of the present invention.
Figure 1B:
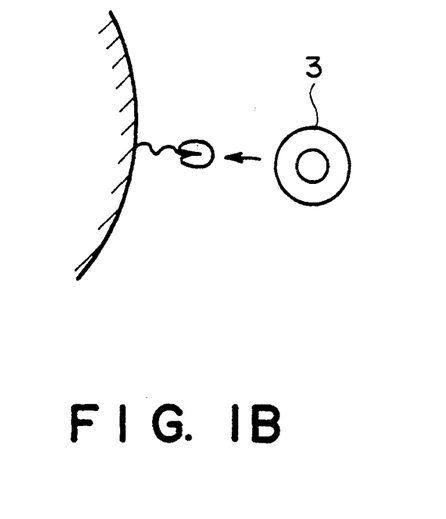
Figure 1C:
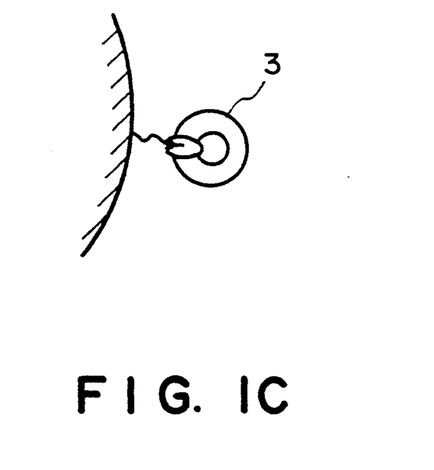
Figure 1D:
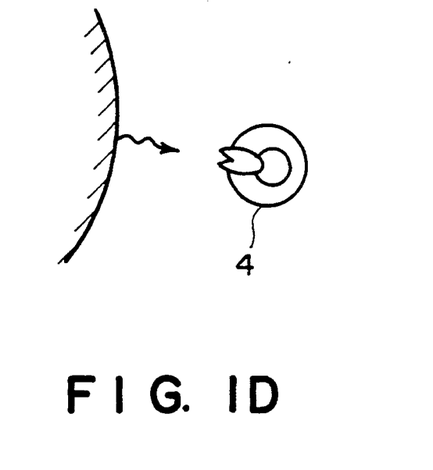
Figure 2A:
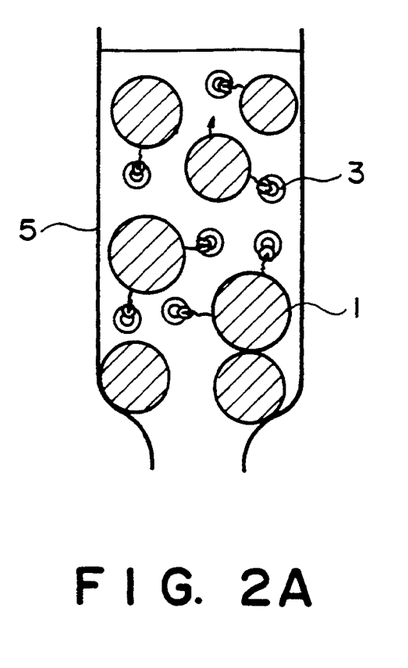
FIGS. 2A and 2B illustrate a method for practicing the present invention by column chromatography.
Figure 2B:
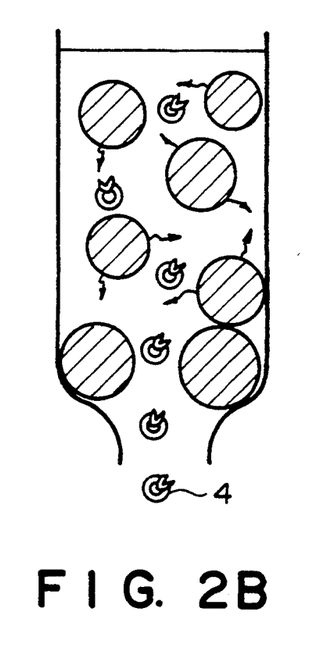
Figure 3:
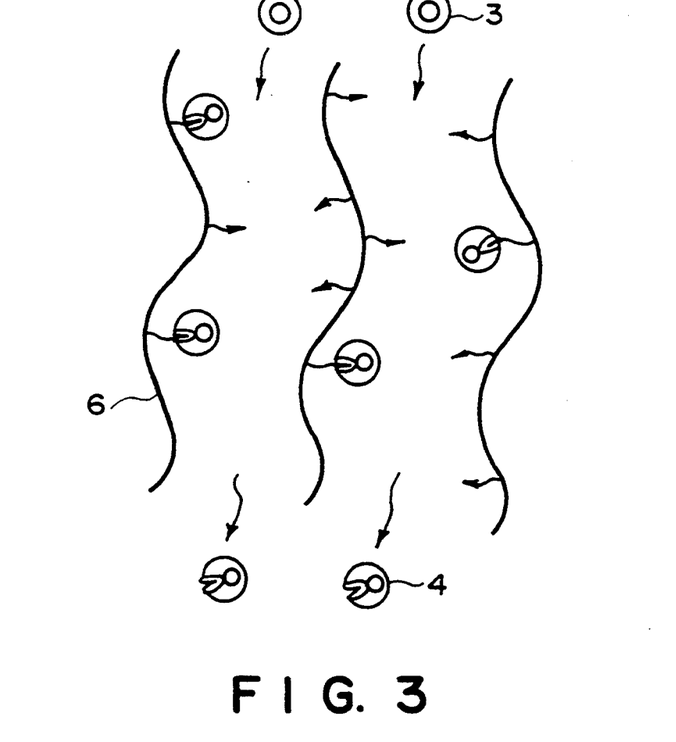
FIG. 3 illustrates a method for practicing the present invention by employing a carrier having a continuous curved surface.

The above formation process may be carried out by use of the carrier 1 packed in a columnar vessel 5 as shown in FIGS. 2A and 2B, or otherwise may be carried out by use of a carrier in a form of a curved membrane sheet 6 as shown in FIG. 3.

According to a second aspect of the present invention, an alkali metal salt solution containing a protein and a lipid is frozen to form a micellar protein-lipid complex dissolved in the solution concentrated by freezing, and subsequent thawing of the frozen salt solution at a room temperature leads to a micelle-lamella transition of the protein-lipid complex to form a bilayer membrane, and the further dialysis against a salt solution or a buffer solution having an osmotic pressure lower than the above salt solution to give a proteoliposome of 5–50 μm diameter, or under a certain condition, of a diameter as large as 300 μm.

Heretofore it was known that a lipid can form a liposome having a bilayer membrane structure through dissolution as micelles into a solution of a detergent, a chaotropic cation, a high concentration of alkali metal salt, or the like, and subsequent removal of the subsidiary substances by dialysis to cause the micelle-lamella transition, sometimes forming a giant liposome having a diameter of as large as 20 μm. The inventors of the present invention found that the addition of a membrane protein and a lipid into a high concentration of an alkali metal salt solution and freezing and thawing the solution will cause incorporation of the membrane protein into the lipid bilayer membrane, and the subsequent dialysis forms giant proteoliposomes having a diameter of 5–300 μm in a large amount, thus having accomplished the present invention.

The protein to be incorporated into the giant proteoliposome in the present invention may be any of the proteins generally known as membrane proteins. The membrane proteins need not necessarily be refined into a pure state. The protein may contain an attached lipid membrane fragment. Proteins other than the membrane protein may be used, provided that the protein has hydrophobic sites at a portion of the surface capable of combining with the membrane.

The material for the lipid in the present invention may be a known amphiphilic compound capable of constituting a monomolecular membrane or a multimolecular membrane. Such a membrane-forming lipid molecule constitutes a long-chain alkyl group having 8 or more carbons and a hydrophilic group. The hydrophilic group may be a cation such as

$$(2C_nN^+2C_1),$$

an anion such as

$$(2C_n\text{-suc-}SO_3^-)$$

a non-ionic compound such as $$(2C_n\text{-gl-}xG)$$

a zwitter ion such as $$(2C_{18}N^+C_1C_2PO_4^-).$$

The examples of the lipids include phospholipids, glycolipids, neutral lipids etc. Further, a non-natural synthetic bilayer-forming lipid may be used. Various additives may be added within the range so that the bilayer structure is not destroyed.

Among the lipid materials, there may be use of glycerophospholipids such as phosphatidylcholine (lecithin), phosphatidylethanolamine, and diphosphatidylglycerol; sphingophospholipids such as sphingomyelin and ceramide ciliatin; sphingoglycolipids such as cerebroside, sulfatide, and ceramide oligohexide; and glycoglycerolipids such as glycosyldiacylglycerol having a carbohydrate as a hydrophilic moiety. Lipid materials in the present invention are not limited to the above examples but any material may be used which Can form lipid bilayer vesicles.

The additives include a membrane-structure reinforcing factor such as cholesterol, and a charge donor such as stearylamine and dicetyl phosphate.

In the formation of a proteoliposome of the present invention, a salt solution is prepared which contains a membrane protein modified by a carrier at a specific site and a membrane lipid.

The salt solution in the present invention contains mainly an alkali metal ion or ions at a high concentration, and may additionally contain other metal ions, an inorganic compound or an organic compound and the like. However, substances exhibiting an antifreezing effect such as sucrose are undesirable. Preferable alkali metals are potassium and rubidium, and sodium may be used. Lithium is not suitable. The salt concentration depends on the kind of the salt: in the case of potassium chloride, high concentration of 2M or higher is desirable. The pH of the solution may be optionally selected within the range so that neither the membrane protein nor the membrane lipid is deactivated.

In the salt solution, the concentration of the membrane protein is such that the ratio of the membrane protein to the lipid is in the range of from 1:1 to 1:200 by weight, preferably 1:10 to 1:120. The concentration of the lipid is usually in the range of 1 to 30 mg/ml, preferably 10 to 20 mg/ml.

Subsequently, the above salt solution is subjected to freezing and thawing, and then to dialysis against another salt solution having an osmotic pressure lower than that of the above salt solution, whereby a giant proteoliposome is prepared.

In freezing the salt solution in the above process, the membrane protein and the membrane lipid form a micellar complex and are dissolved into the solution concentrated by freezing. In the subsequent thawing of the frozen salt solution at room temperature, the protein-lipid complex undergoes micelle-lamella transition to form a bilayer membrane, and further by dialysis of the salt solution against a salt solution having a lower osmotic pressure, it forms proteoliposomes usually having a diameter of 5 to 50 $\mu$m, in a certain condition, having a diameter of 300 $\mu$m.

The repetition of the freezing and thawing is preferably three times or more, but 6 times of repetition is sufficient. Agitation by means of a vortex mixer after the freezing-thawing is desirable.

The salt solution used for dialysis may be a solution of alkali metal salt or an alkaline earth metal at a concentration of 0.1 to 100 mM, preferably from 1 to 20 mM.

The third aspect of the present invention is a combination of the first aspect and the second aspect of the invention, and relates to a method of preparing a membrane giant proteoliposome, comprising the steps of modifying a membrane protein at specific sites thereof with a carrier; preparing a salt solution containing the membrane protein and a membrane lipid: freezing and thawing the salt solution; and dialyzing the salt solution with a second salt solution having a lower osmotic pressure than the above solution.

The invention also relates to a method of preparing a giant proteoliposome, comprising the steps of combining a membrane protein with a carrier; preparing a salt solution containing the membrane protein combined with the carrier and a membrane lipid to form a proteoliposome; freezing and thawing the salt solution; dialyzing the salt solution with a second salt solution having a lower osmotic pressure than the above salt solution; and then dissociating the membrane protein from the carrier.

The giant proteoliposome formed according to the present invention has a diameter as large as from 5 to 300 $\mu$m. In the case where the diameter of the giant proteoliposome distributes in a certain range, the carrier should preferably have a volume equal to or larger than the the proteoliposome to be formed in order to limit the orientation of all the incorporated proteins. The shape of the carrier is, for example, spherical as mentioned above, and the size is equal to or larger than the diameter of the proteoliposome to be formed, or otherwise planar or curved and the radius of the curvature is equal to or larger than the radius of the liposome for the proteoliposome to be formed.

The spherical carrier, for example, has a diameter of at least 100 $\mu$m, and more preferably 300 $\mu$m or more in consideration of the modification efficiency of the protein and the void for proteoliposome formation. A carrier for cell affinity chromatography having a diameter exceeding 300 $\mu$m is commercially available for this purpose.

The shape of the carrier is not necessarily spherical but may be of any shape. Specific examples of planar or curved carriers are those in a plate structure or a laminated plate structure having on the surface thereof an active group for combining with a protein, or having the surface capable of accepting a donated active group. For example, 1 mm square fragments of a cellulose type membrane filter or of nitrocellulose membrane for dialysis use are preferably employed for modifying a specific portion of the membrane protein since the hydroxyl groups on the surface thereof can be activated as desired by cyanogen bromide, etc. Porous glass plates having large pore size (larger than 100 $\mu$m) are also employed as a carrier exhibiting high efficiency of membrane protein modification.

The membrane protein is modified by and dissociated from the carrier as mentioned above.

The examples below illustrate the present invention more specifically.

EXAMPLE 1

Bovine rhodopsin was isolated and purified by the procedure shown below. The operation was conducted entirely under dark red light (with Red Filter No. 1 of Eastman Kodak Co.).

From a bovine retina, a disc, which is a membrane-constituting material containing rhodopsin, was isolated and purified according to the Ficoll flotation method (Smith et al.: Exp. Eye Res. 20, 211–217 (1975)). The purified disc was solubilized by the solution consisting of 50 mM octyl glucoside, 0.1M NaCl, 1 mM $MnCl_2$, 1 mM $CaCl_2$, and 10 mM Mops-NaOH (pH 7.0), and then the rhodopsin was purified by affinity chromatography employing a column (5 mm × 10 cm) of Con A-Sepharose 4B; agarose gel (supplied by Pharmacia Co., average gel particle diameter: ca. 100 $\mu$m). More specifically, the solubilized disc, in an amount of 5 mg as protein, was added to the column to combine the rhodopsin with concanavalin A, and then the column was washed sufficiently with a buffer solution (0.1M NaCl, 1 mM $MnCl_2$, 1 mM $CaCl_2$, 10 mM Mops-NaOH (pH 7.0)) to eliminate impurities. The rhodopsin having been combined through concanavalin A with the carrier gel particles was used, as it is, for forming proteoliposome.

On the other hand, a liposome was formed as below by a freeze-thaw method. A thin film of 15 mg of asolectin (soy bean phosphatIdylcholine, type IV S, supplied by Sigma Co.) was formed on the inside wall of a test tube of 10 × 130 mm. Thereto 1 ml of a solution of 0.1M NaCl, 10 mM Mops-NaOH (pH 7.0) was added and treated by a vortex mixer for 1 minute (at highest power level) to disperse the lipid thin membrane. The lipid dispersion was transferred into a polypropylene tube (12 × 75 mm: Becton Dickinson Co.: Falkon ® 2063) provided with a cap and was saturated with nitrogen. It was subjected to sonication treatment with a waterbath-type sonicator (made by Branson Co.: Sonifier B-15 (200 W), with cup-horn) for 40 minutes (at power level 2, duty cycle 60%, water-cooled) to give a sonicated liposome dispersion having an average particle diameter of 100 nm or less.

This liposome dispersion was subjected to the three cycles of treatments comprising freezing by dry ice-acetone bath, thawing at room temperature, and treatment by water-bath-type sonication apparatus for 30 seconds (at power level 1), thus giving the intended liposome dispersion (average diameter: ca 1 μm, volume: 0.5 μm$^3$).

The liposome dispersion was added to the above column, and was incubated at room temperature for 1 hour to incorporate the rhodopsin into the liposome and to form proteoliposome.

Subsequently, for the purpose of dissociating the rhodopsin from the carrier and eluting the proteoliposome from the column, a buffer solution (50 mM methyl-α-D-mannoside, 50 mM methyl-α-D-glucoside, 0.1M NaCl, 10 mM Mops-NaOH (pH 7.0)) was made to glow through the column which contains methyl-α-D-mannoside and methyl-α-D-glucoside capable of combining with the sugar chain of the rhodopsin antagonistically to concanavalin A. The solution leaving the column was collected, and was dialyzed against a buffer solution (0.1M NaCl, 10 mM Mops-NaOH (pH 8.0)) to eliminate free sugar molecules.

The incorporation of the rhodopsin into the resultant proteoliposome membrane was confirmed as below. The proteoliposome liquid dispersion was frozen by a liquid helium rapid-freeze apparatus (Eiko Engineering Co.: RF-23), and the replica of the membrane surface prepared by a freeze-fracture replica preparation apparatus (Eiko Engineering Co.:FD-5A) was observed by a transmission type electron microscope (JEOL, Ltd.: JEM 100U). Particle of about 4 nm diameter were observed, which proves the incorporation of rhodopsin.

β-N-acetylglucosaminidase (Sigama Co.) was reacted with the proteoliposome liquid dispersion. As a result, free sugar was detected in the external liquid, which proves that the sugar residue is incorporated toward the outside of the proteoliposome.

EXAMPLE 2

A purple membrane, a membrane fragment containing bacteriorhodopsin, was obtained by extraction from a hyperhalophilic Halobacterium halobium according to the method of P. Oesterhelt and W. Stoeckenius (Methods of Enzymology, 31, 667–678 (1974)). The purple membrane was delipidated according to the method of K. S. Huang et al. (Proceedings of National Academy of Science, USA, 77 323 (1980)) to purify the bacteriorhodopsin.

A monoclonal antibody which will specifically combine with the carboxyl ends of the bacteriorhodopsin was prepared according to the method of K. Kimura (J. Biol. Chem. 257, 2859–2867 (1980)). This monoclonal antibody specifically combines with fragments comprising 39 residues having carboxyl ends from among the peptide fragments obtained by cyanogen bromide treatment of the bacteriorhodopsin.

This CNBr-6 monoclonal antibody was immobilized by a covalent bond onto the CNBr-activated Sepharose 4B, an agarose gel supplied by Pharmacia Co. (gel particle diameter: approximately 100 μm) at a ratio of 2 mg of the antibody per ml of the swelled gel. It was reacted overnight at the condition of the coupling buffer of 0.5M NaCl, 0.2M NaHCO$_3$ (pH 8.5) at 4° C. The unreacted active groups were blocked. and then the excess of antibody was washed off. The gel having combined with the antibody was put into a column of 5 mm×10 cm, which was washed with 0.1M NaCl.

A 0.1M NaCl solution containing 0.2 mg of purified bacteriorhodopsin was made to flow in the column to combine the carboxyl ends of the bacteriorhodopsin with the CNBr-6 monoclonal antibody immobilized on the gel.

A liposome liquid dispersion was prepared in the same manner as in Example 1.

The liposome suspension was added to the column which had 0.2 mg of immobilized bacteriorhodopsin, and was incubated for one hour to incorporate the bacteriorhodopsin into the liposome.

Through the column, 0.1M NaCl which was adjusted to pH11 with ammonia was made to flow to dissociate the bacteriorhodopsin from CNBr-6 monoclonal antibody and to elute the proteoliposome. The proteoliposome having been eluted was immediately dialyzed against 0.1M NaCl. Approximately 40% of the bacteriorhodopsin was recovered as incorporated in the proteoliposome.

The proteoltposome prepared by the above procedure incorporated the bacteriorhodopsin with the carboxyl end directing outside, which was confirmed by pH change of the external liquid to alkaline side on light irradiation of the proteoliposome suspension, and the formation of peptides having carboxyl ends as the digested product upon enzymatic treatment of the proteoliposome.

EXAMPLE 3

Bacteriorhodopsin and CNBr-6 monoclonal antibody were prepared by the methods described in Example 2. A liposome liquid dispersion was prepared in the method described in Example 1.

A cellulose type membrane filter (pore diameter: 0.22 μm) supplied by Millipore Co. was employed as a planar carrier. The filter was cut into small pieces of about 1 mm square, and was subjected to cyanogen bromide treatment to activate the hydroxyl group on the surface so that it can combine with a protein having amino groups. To this membrane filter, the CNBr-6 monoclonal antibody prepared as above was added in an amount of 1 mg per 100 mg of the membrane filter, and was made to react to combine the monoclonal antibody with the filter. The excess antibody was removed by washing.

The membrane filter having the combined monoclonal antibody (dry weight: 10 mg, 0.1 mg as monoclonal antibody) was added to 1 ml of a 0.1M NaCl solution containing 0.2 mg of the purified bacteriorhodopsin to combine the carboxyl ends of the bacteriorhodopsin with the CNBr-6 monoclonal antibody immobilized on the membrane filter. Then the membrane filter was washed with 0.1M NaCl to remove free protein, and was added to the liposome dispersion prepared as above, which was incubated for one hour to incorporate the bacteriorhodopsin into the liposome.

Subsequently, the pH of the dispersion was adjusted to 11 by adding 1N aqueous ammonia to dissociate the bacteriorhodopsin from the antibody. Thereafter, the dispersion was made neutral by adding 1N hydrochloric acid, and the membrane filter was removed by centrifugation.

The recovery ratio of the bacteriorhodopsin was approximately 20%.

The proteoliposome prepared by the above procedure incorporated the bacteriorhodopsin with the carboxyl ends directing outside, which was confirmed by pH change of the external liquid to alkaline side on light irradiation of the proteoliposome suspension, and formation of peptides having carboxyl ends as the digested product on enzymatic treatment of the proteoliposome.

EXAMPLE 4

A method for introducing bacteriorhodopsin into a lipid bilayer membrane in a uniform orientation is shown by employing an affinity chromatographic column in which an anti-bacteriorhodopsin antibody is immobilized as a ligand to a cyanogen-bromide-activated agarose carrier.

The bacteriorhodopsin was prepared by extracting a purple membrane from a hyperhalophilic bacteria, Halobacteriuan halobium, according to the method of P. Oesterhelt and W. Stoeckenius (Method. Enzymol. 31, 667–678 (1974)), and delipidating it according to the method of K. S. Huang, et al. (Proc. Natl. Acad. Sci. USA, 77, 323 (1980)).

A monoclonal antibody which specifically combines with the carboxyl end of the bacteriorhodopsin was prepared according to the method of K. Kimura (J. Biol. Chem. 257, 2859–2867 (1980)). This monoclonal antibody specifically combines with fragments comprising 39 residues having carboxyl ends from among the peptide fragments obtained by cyanogen bromide treatment of the bacteriorhodopsin.

This CNBr-6 monoclonal antibody was immobilized by a covalent bond on the CNBr-activated Sepharose 4B, an agarose gel supplied by Pharmacia Co. at a ratio of 2 mg of the antibody per ml of the swelled gel. It was made to react overnight at the condition of the coupling buffer of 0.5M NaCl, 0.2M NaHCO$_3$ (pH 8.5) at 4° C. The unreacted active groups were blocked, and then excess of antibody was washed off. Then the gel was washed with 0.1M NaCl.

A 0.1M NaCl solution containing 0.2 mg of purified bacteriorhodopsin was made to flow in the column to combine the carboxyl end of the bacteriorhodopsin with the CNBr-6 monoclonal antibody immobilized on the gel. The gel was washed again with 0.1M NaCl to remove unreacted bacteriorhodopsin.

A thin film of 15 mg of soy bean phospholipid (asolectin) was hydrated in 1 ml of 0.1M NaCl by means of a vortex mixer, and was treated by means of a Probe type sonicator for 30 minutes. It was mixed with a gel having the combined bacteriorhodopsin. The mixture was subjected to three cycles of treatments comprising freezing in dry ice-acetone, thawing at room temperature, and mild sonication treatment, giving a proteoliposome incorporated with bacteriorhodopsin.

The pH of the mixture was adjusted to 11 by addition of 0.1N aqueous ammonia to dissociate the bacteriorhodopsin incorporated in the liposome from the CNBr-6 monoclonal antibody. The proteoliposome was separated from the carrier gel, and the mixture was made neutral again. Finally, the proteoliposome was collected by centrifugation.

The proteoliposome prepared by the above procedure incorporated the bacteriorhodopsin with the carboxyl ends directed outside, which was confirmed by pH change of the external liquid to alkaline side on light irradiation of the proteoliposome suspension, and formation of peptide having carboxyl ends as the digested product upon enzymatic treatment of the proteoliposome.

EXAMPLE 5

Soy bean phospholipid (asolectin) corresponding to 15 mg of lipid dissolved in chloroform was placed in a test tube of 10 mm in diameter and about 130 mm in length. The solvent was evaporated off by means of a rotary evaporator, and further the solvent was completely removed in a desiccato in vacuo. Thereto, 1 ml of 3M aqueous potassium chloride solution which had been adjusted to a certain pH by addition of an aqueous hydrochloric acid or an aqueous potassium hydroxide solution was added. It was treated in a vortex mixer for 30 seconds to disperse the lipid thin membrane, and then was treated by a probe type sonicator for 30 minutes, giving a suspension of unilamellar liposome having a diameter of 100 μm.

A membrane protein was added to the liposome suspension. Bacteriorhodopsin was used as an example of the membrane protein for forming a proteoliposome. The bacteriorhodopsin was prepared by extracting a purple membrane from a hyperhalophilic bacteria, Halobacterium halobium, according to the method of P. Oesterhelt and W. Stoeckenius (Method. Enzymol. 31, 667–678 (1974)) and delipidating it according to the method of K. S. Huang, et al. (Proc. Natl. Acad. Sci. USA, 77, 323 (1980)). The bacteriorhodopsin was added to the liposome suspension in a ratio of lipid to protein within a range of from 40 to 200 by weight.

The suspension was subjected to three cycles of the treatments comprising freezing by liquid nitrogen or dry ice-acetone, thawing at room temperature, and vortex mixer treatment for 30 seconds. The suspension was then transferred to a dialysis tube, and subjected to dialysis against 10 mM aqueous potassium chloride solution for 2 days. Thus a giant proteoliposome having a diameter exceeding 10 μm was prepared in a large amount.

The diameter of the resultant proteoliposome depends on the pH during the preparation. In the case where the preparation operation was conducted at the pH within 3 to 11 from beginning to freezing and thawing, the diameter was within the range of about 5 to 50 μm, most of the particles having diameter of about 20 to 30 μm, while in the case where the operation was performed below pH 2, the particle size was distributed non-uniformly over a broad range of from about 5 to 300 μm.

In order to test whether the incorporated protein retained the inherent function without being denatured nor inactivated in the prepared proteoliposome, the suspension of the giant proteoliposome having the incorporated bacteriorhodopsin was exposed to light of 560 nm, and the change of pH in the external liquid was measured. When the suspension of the giant proteoliposomes was irradiated with light, through a suitable filter, coming from a halogen light source, pH in the external liquid changed independently of the pH in the preparation step (in most cases, to alkaline side), from which the bacteriorhodopsin was confirmed to be incorporated with retention of its function.

EXAMPLE 6

A thin film of 15 mg of asolectin (soy bean phosphatidylcholine, type IV S, supplied by Sigma Co.) was formed on the inside wall of a test tube of 10×130 mm.

Thereto 1 ml of a solution of 3M KCl, 50 mM $MgCl_2$, 1M Hepes-KOH (pH 7.5) was added and treated by a vortex mixer for 1 minute (at highest power level) to disperse the lipid thin membrane. The lipid dispersion was transferred into a polypropylene tube (12×75 mm; Becton Dickinson Co.: Falkon ® 2063) provided with a cap and was saturated with nitrogen. It was subjected to sonication treatment with a water-bath-type sonicator (made by Branson Co.: Sontrier B-15 (200 W), with cup-horn) for 40 minutes (at power level 2, duty cycle 60%, water-cooled) to give a liposome liquid dispersion.

A human erythrocyte sugar transporting protein was prepared according to the method of M. Kasahara and P. C. Hinkle, (J. Biol. Chem. 252, 7384 (1977). 40 μg of the preparation after removing the detergent was added to the previously prepared liposome liquid dispersion, which was subjected to a mild sonication treatment by means of a water-bath-type sonicator. Subsequently, the mixture was subjected to three cycles of treatments comprising freezing in a dry ice-acetone bath, thawing at room temperature, and dispersing by a vortex mixer. The liquid dispersion thus prepared was dialyzed for 2 days against 2 liters of 2 mM $MgCl_2$, 10 mM Hepes-KOH (pH 7.5), and observed by a phase contrast microscope. It was found that a large number of giant proteoliposomes having diameters exceeding 10 μm had formed.

The giant proteoliposome liquid dispersion was frozen rapidly by a liquid helium rapid-freeze apparatus (Eiko Engineering Co.: RF-23), and the replica of the membrane surface prepared by a freeze-fracture replica preparation apparatus (Eiko Engineering Co.:FD-SA) was observed by a transmission type electron microscope (JEOL, Ltd.: JEM 100U). Particles of about several nm in diameter were observed, which proves directly the incorporation of the protein into the giant proteoliposome membrane.

EXAMPLE 7

A purple membrane, a membrane fragment containing bacteriorhodopsin, was obtained by extraction from a hyperhalophilic Halobacterium halobium according to the method of P. Oesterhelt and W. Stoeckenius (Methods of Enzymology, 31, 667–678 (1974)). The purple membrane was delipidated according to the method of K. S. Huang (Proceedings of National Academy of Science, USA, 77, 323 (1980)) to purify the bacteriorhodopsin.

A monoclonal antibody which will specifically combine with the carboxyl ends of the bacteriorhodopsin was prepared according to the method of K. Kimura (J. Biol. Chem., 257, 2859–2867 (1980)). This monoclonal antibody specifically combines with fragments comprising 39 residues having carboxyl ends from among the peptide fragments obtained by cyanogen bromide treatment of the bacteriorhodopsin.

A cellulose type membrane filter (pore diameter: 0.22 μm) supplied by Millipore Co. was cut into small pieces of about 1 mm square, and was subjected to cyanogen bromide treatment to activate the hydroxyl group on the surface so that it can combine with a protein having amino groups. To this membrane filter, the CNBr-6 monoclonal antibody prepared as above was added in an amount of 1 mg per 100 mg of the membrane filter, and was made to react to combine the monoclonal antibody with the filter. The excess antibody was removed by washing.

Separately, 15 mg of soy bean phospholipid dissolved in chloroform was placed in a test tube. The solvent was evaporated off by means of a rotary evaporator and a vacuum pump, to form a thin film of the lipid on the wall of the test tube. Thereto 1 ml of 3M KCl solution (pH 8.0) was added. The lipid was suspended by a vortex mixer, and the solution was treated by a probe type sonicator, giving a dispersion of liposome having a diameter of 100 nm or less.

To this liposome dispersion, the small pieces of the membrane filter having monoclonal antibody combined were added. The suspension was subjected to three cycles of the treatments comprising freezing by liquid nitrogen or dry ice-acetone, thawing at room temperature, and vortex mixer treatment for 30 seconds. The suspension was then transferred to a dialysis tube, and subjected to dialysis against 10 mM aqueous potassium chloride solution for 2 days, thus forming a large number of giant proteoliposomes having a diameter exceeding 10 μm.

The giant proteoliposome prepared by the above procedure incorporated the bacteriorhodopsin with the carboxyl end directing outside, which was confirmed by pH change of the external liquid to alkaline side on light irradiation to the proteoliposome suspension, and formation of peptide having carboxyl ends as the digested product on enzymatic treatment of the proteoliposome.

EXAMPLE 8

A giant proteoliposome was prepared in the same manner as in Example 7. The pH of the proteoliposome was made to be 11 by adding 1N aqueous ammonia to dissociate the bacteriorhodopsin incorporated into the liposome from the CNBr-6 monoclonal antibody, thus forming a giant proteoliposome having a diameter exceeding 5 μm.

The giant proteoliposomes prepared by the procedure above incorporated the bacteriorhodopsin with the carboxyl ends directing outside, which was confirmed by pH change of the external liquid to alkaline side on light irradiation to the proteoliposome suspension, and formation of peptide having carboxyl ends as the digested product on enzymatic treatment of the proteoliposome.

EXAMPLE 9

Bovine rhodopsin was isolated and purified by the procedure shown below. The operation was all conducted under dark red light (with Red filter No. 1 of Eastman Kodak Co.).

From a bovine retina, a disc which is a membrane constituting material containing rhodopsin was isolated and purified according to the Ficoll flotation method (Smith et al.: Exp. Eye Res. 20, 211–217 (1975)). The purified disc was solubilized by the solution consisting of 50 mM octyl glucoside, 0.1M NaCl, 1 mM $MnCl_2$, 1 mM $CaCl_2$, and 10 mM Mops-NaOH (pH 7.0), and then the rhodopsin was purified by affinity chromatography employing wheat germ Lectin-Sepharose 6MB; agarose gel, (supplied by Pharmacia Co., average gel particle diameter: ca. 300 μm) by batchwise treatment (wet volume of 2 ml). More specifically, the gel, in an amount of 5 mg as protein, was added to the solution of the solubilized disc, combined the rhodopsin with the lectin, and then the gel was washed sufficiently with a buffer solution (0.1M NaCl, 1 mM $MnCl_2$, 1 mM $CaCl_2$, 10 mM Mops-NaOH (pH 7.0)) to eliminate impurities.

The rhodopsin having been combined through the lectin with the carrier gel particles was used, as is, for forming proteoliposome.

Separately, 15 mg of soy bean phospholipid dissolved in chloroform was placed in a test tube. The solvent was evaporated off by means of a rotary evaporator and a vacuum pump to form a thin film of the lipid on the wall of the test tube. Thereto 1 ml of a solution of 3M NaCl, 1 mM $MnCl_2$, 1 mM $CaCl_2$, and 0.1M Mops-NaOH (pH 7.0) were added, and suspended by a vortex mixer, and the suspension was treated by a probe type sonicator, giving a dispersion of liposome having a diameter of 100 nm or less.

The gel having rhodopsin combined was added to the liposome liquid dispersion and mildly stirred for 30 minutes. The suspension was subjected to three cycles of the treatments comprising freezing by liquid nitrogen or dry ice-acetone, thawing at room temperature, and mixing by vortex mixer for 30 seconds. The suspension was then transferred to a dialysis tube, and was dialyzed against a solution of $\beta$-N-acetylglucosaminidase (Sigma Co.) reacted with the giant proteoliposome liquid dispersion.

To 1 ml of the dispersion, 2 ml of a solution 10 mM NaCl, 10 mM Mops-NaOH (pH 7.0) for 2 days, thus forming a large number of giant proteoliposomes having a diameter exceeding 10 $\mu$m.

To 1 ml of the dispersion, 2 ml of a solution of 20 mM N-acetyl-$\alpha$-D-glucosamine, 10 mM NaCl, and 10 mM Mops-NaOH (pH 7.0) was added, and was incubated for one hour in order to dissociate the rhodopsin from the carrier and to separate the proteoliposome from the carrier. The giant liposome dispersion was recovered as the supernatant. Further the dispersion was dialyzed against a solution of 10 mM NaCl, 10 mM Mops-NaOH (pH 7.0) to remove N-acetyl-$\alpha$-D-glucosamine. The yield was approximately 30% in terms of protein.

The incorporation of the rhodopsin into the resultant proteoliposome membrane was confirmed as below. The proteoliposome liquid dispersion was frozen by a liquid helium rapid-freeze apparatus (Eiko Engineering Co.: RF-23), and the replica of the membrane surface prepared by a freeze-fracture replica preparation apparatus (Eiko Engineering Co.:FD-5A) was observed by a transmission type electron microscope (JEOL, Ltd.: JEM 100U). Particle of about 4 nm diameter were observed, which proves the incorporation of rhodopsin.

$\beta$-N-acetylglucosaminidase (Sigma Co.) reacted with the giant proteoliposome liquid dispersion. As the result, free sugar was detected in the external liquid, which proves that the sugar residue is incorporated toward the outside of the proteoliposome.

In the present invention as described above, in forming a proteoliposome by incorporating a membrane protein into a liposome, the orientation of the protein relative to the interior and exterior of a vesicle membrane can be controlled. Therefore, incorporation of a membrane protein, having a function of transporting a substance in one direction through the membrane such as a substance transporting ATPase, membrane allows the control of the substance transfer direction from the interior to the exterior of the vesicle or the reverse direction, which remarkably increases the efficiency of the substance transfer since inappropriate protein orientation is decreased and the required amount of the inappropriate protein is decreased.

Further, a protein such as an enzyme and an antibody which can combine specifically with a substrate or an antigen-antibody and so forth is made possible to be embedded membrane, and the embedding can be made in such an orientation that the combining sites are directed toward the exterior of the liposome, so that the unsuitably orienting protein may be decreased, and the required amount of the protein can be reduced.

As described above, the present invention has made it possible to prepare a large amount of giant proteoliposomes having a diameter of 5 $\mu$m or larger in a simple procedure under mild conditions without deactivation nor denaturation of the protein, which could not be achieved practically by prior art.

Additionally, the present invention has achieved, in formation of a giant proteoliposome, the advantage of controlling the orientation of the membrane protein incorporated into the giant proteoliposome.

We claim:

1. A method for preparing a giant proteoliposome, comprising freezing and thawing an alkali metal salt solution containing a membrane protein and a lipid, and subsequently dialyzing against a second salt solution or a buffer solution having a lower osmotic pressure than that of said alkali metal salt solution to form a giant proteoliposome having a diameter of 5 $\mu$m or more.

2. A method for preparing a giant proteoliposome, comprising freezing and thawing an alkali metal salt solution containing a membrane protein combined with a carrier that will not enter a lipid larger of a liposome and a lipid, and subsequently dialyzing against a second salt solution or a buffer solution having a lower osmotic pressure than that of said alkali metal salt solution to form a giant proteoliposome having a diameter of 5 $\mu$m or more.

3. A method for preparing a giant proteoliposome, comprising freezing and thawing an alkali metal salt solution containing a membrane protein combined with a carrier that will not enter a lipid layer of a liposome and a lipid, and subsequently dialyzing against a second salt solution or a buffer solution having a lower osmotic pressure than that of said alkali metal salt solution and thereafter separating said membrane protein from said carrier to form a giant proteoliposome having a diameter of 5 $\mu$m or more.

4. The method of claim 2 or 3, wherein the volume of said carrier is equal to or larger than the volume of said giant proteoliposome.

5. The method of claim 2 or 3, wherein the shape of said carrier is spheric and the diameter thereof is equal to or larger than the diameter of said giant proteoliposome.

6. The method of claim 2 or 3, wherein the shape of said carrier is planar or curved, and the radius of curvature thereof is equal to or larger than the radius of said giant proteoliposome.

7. The method of claim 2 or 3, wherein said carrier is combined with hydrophilic side chains of said membrane protein.

8. A method for forming a proteoliposome, comprising freezing and thawing an alkali metal salt solution containing a membrane protein combined with a carrier that will not enter a lipid layer of a liposome and a lipid to incorporate said membrane protein into said liposome.

9. The method of claim 8, wherein the volume of said carrier is equal to or more than the volume of said liposome.

10. The method of claim 8, wherein the shape of said carrier is spheric and the diameter thereof is equal to or larger than the diameter of said liposome.

11. The method of claim 8, wherein the shape of said carrier is planar or curved, and the radius of curvature thereof is equal to or larger than the radius of said liposome.

12. The method of claim 8, wherein said carrier is combined with hydrophilic side chains of said membrane protein.

13. The method of claim 8, wherein said membrane protein incorporated into said liposome subsequently separated from said carrier.

* * * * *

UNITED STATES PATENT AND TRADEMARK OFFICE
CERTIFICATE OF CORRECTION

PATENT NO. : 5,374,715
DATED : December 20, 1994
INVENTOR(S) : TSUNEHIRO KANNO, ET AL.

Page 1 of 3

It is certified that error appears in the above-indentified patent and that said Letters Patent is hereby corrected as shown below:

ON TITLE PAGE

In [56] References Cited, under OTHER PUBLICATIONS:
"In "Reconstituted ... etc.", "fromt he" should read --from the-- and "Concanavalin A,"" should read --Concanavalin A$^+$,"--.

COLUMN 4

Line 4, "Giant" should read --giant--.

COLUMN 5

Line 7, "proteollposome" should read --proteoliposome--.
Line 22, "enzyme:" should read --enzyme;--.

COLUMN 6

Line 57, "llposome" should read --liposome--.

COLUMN 8

Line 58, "Can" should read --can--.
Line 59, "bilaver" should read --bilayer--.

COLUMN 10

Line 59, "phosphatldylcholine" should read --phosphatidycholine--.

UNITED STATES PATENT AND TRADEMARK OFFICE
CERTIFICATE OF CORRECTION

PATENT NO. : 5,374,715
DATED : December 20, 1994
INVENTOR(S) : TSUNEHIRO KANNO, ET AL.

Page 2 of 3

It is certified that error appears in the above-indentified patent and that said Letters Patent is hereby corrected as shown below:

COLUMN 11

Line 21, "glow" should read --flow--.

COLUMN 12

Line 18, "pH11" should read --pH 11--.
Line 24, "teollposome" should read --teoliposome--.
Line 25, "proteoltposome" should read --proteoliposome--.

COLUMN 13

Line 8, "carboxyl" should read --carboxyl--.

COLUMN 14

Line 11, desiccato" should read --desiccator--.

COLUMN 16

Line 31, "proteollposome" should read --proteoliposome--.

COLUMN 17

Line 21, "ß-N-acetylglucosaminidase" should be deleted.
Lines 22-23 should be deleted.
Line 24, "To 1 ml of the dispersion, 2 ml of a solution" should be deleted.

COLUMN 18

Line 5, "orlenting" should read --orienting--.
Line 29, "larger" should read --layer--.

UNITED STATES PATENT AND TRADEMARK OFFICE
CERTIFICATE OF CORRECTION

PATENT NO. : 5,374,715
DATED : December 20, 1994
INVENTOR(S) : TSUNEHIRO KANNO, ET AL.

It is certified that error appears in the above-indentified patent and that said Letters Patent is hereby corrected as shown below:

<u>COLUMN 20</u>

Line 5, "liposome" should read --liposome is--.

Signed and Sealed this

Twenty-fifth Day of April, 1995

*Attest:*

BRUCE LEHMAN

*Attesting Officer*   Commissioner of Patents and Trademarks